(12) United States Patent
Suzuki (10) Patent No.: US 11,291,350 B2
(45) Date of Patent: Apr. 5, 2022

(54) MEDICAL DEVICE INCLUDING A PATIENT CIRCUIT CONTROLLED BY A SECONDARY CIRCUIT THAT DETECTS ERRONEOUS TRANSMISSION

(71) Applicant: Sony Olympus Medical Solutions Inc., Tokyo (JP)

(72) Inventor: Takashi Suzuki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 453 days.

(21) Appl. No.: 16/259,057

(22) Filed: Jan. 28, 2019

(65) Prior Publication Data

US 2019/0274519 A1 Sep. 12, 2019

(30) Foreign Application Priority Data

Mar. 6, 2018 (JP) .............................. JP2018-039946

(51) Int. Cl.
*A61B 1/00* (2006.01)
*G16H 30/40* (2018.01)
(Continued)

(52) U.S. Cl.
CPC ...... *A61B 1/00011* (2013.01); *A61B 1/00009* (2013.01); *A61B 1/00112* (2013.01);
(Continued)

(58) Field of Classification Search
None
See application file for complete search history.

(56) References Cited

U.S. PATENT DOCUMENTS

| 4,298,260 | A | * | 11/1981 | Takayama | ............... | A61B 1/045 |
| | | | | | | 396/155 |
| 5,060,632 | A | * | 10/1991 | Hibino | ................. | A61B 1/0052 |
| | | | | | | 600/109 |

(Continued)

FOREIGN PATENT DOCUMENTS

| JP | 2-193634 | 7/1990 |
| JP | 7-86633 A | 3/1995 |

(Continued)

OTHER PUBLICATIONS

Japanese Office Action dated Jan. 11, 2022, in corresponding Japanese Patent Application No. 2018-039946.

*Primary Examiner* — Michael J Carey
*Assistant Examiner* — Minqiao Huang
(74) *Attorney, Agent, or Firm* — Xsensus LLP (57) ABSTRACT

A disclosed medical device includes a first data transmission path that includes a first insulation device connecting a secondary circuit and a patient circuit such that serial data output from the secondary circuit is transmitted to the patient circuit while maintaining electrical insulation between the secondary circuit and the patient circuit; a second data transmission path that includes a second insulation device connecting the secondary circuit and the patient circuit such that the serial data transmitted from the secondary circuit to the patient circuit via the first data transmission path is fed back to the secondary circuit while maintaining electrical insulation between the secondary circuit and the patient circuit; and a comparison determination unit that is provided in the secondary circuit and compares the serial data output from the secondary circuit with the serial data fed back to the secondary circuit.

17 Claims, 5 Drawing Sheets

(51) Int. Cl.
  *G06F 1/18* (2006.01)
  *G06F 1/26* (2006.01)
  *G06F 1/16* (2006.01)
  *G06F 13/38* (2006.01)
  *A61B 1/05* (2006.01)

(52) U.S. Cl.
  CPC ............ *G06F 1/1686* (2013.01); *G06F 1/182* (2013.01); *G06F 1/266* (2013.01); *G06F 13/38* (2013.01); *G16H 30/40* (2018.01); *A61B 1/0002* (2013.01); *A61B 1/05* (2013.01)

(56) References Cited

U.S. PATENT DOCUMENTS

| | | | | |
|---|---|---|---|---|
| 5,241,260 | A * | 8/1993 | Beland | H02M 7/1557 323/270 |
| 5,543,831 | A * | 8/1996 | Tsuji | H04N 7/183 128/901 |
| 5,900,683 | A * | 5/1999 | Rinehart | H03K 17/18 307/129 |
| 6,184,922 | B1 * | 2/2001 | Saito | A61B 1/00114 348/65 |
| 6,366,957 | B1 * | 4/2002 | Na | G06F 21/575 709/229 |
| 7,129,472 | B1 * | 10/2006 | Okawa | A61B 1/00059 250/234 |
| 8,463,394 | B2 * | 6/2013 | Forsell | A61N 1/3787 607/61 |
| 2008/0009744 | A1 * | 1/2008 | Misono | B06B 1/0215 600/462 |
| 2009/0105540 | A1 * | 4/2009 | Kawata | A61B 1/00006 600/118 |
| 2009/0116265 | A1 * | 5/2009 | Saji | H02M 3/33507 363/37 |
| 2010/0022828 | A1 * | 1/2010 | Ono | A61B 1/00036 600/109 |
| 2010/0292573 | A1 * | 11/2010 | Tanaka | B06B 1/0253 600/439 |
| 2011/0201871 | A1 * | 8/2011 | Forsell | A61B 1/04 600/16 |
| 2012/0127294 | A1 * | 5/2012 | Yamaguchi | H04N 7/183 348/73 |
| 2012/0178992 | A1 * | 7/2012 | Fujimoto | H04N 7/183 600/109 |
| 2012/0212251 | A1 * | 8/2012 | Yanagishima | H03K 17/691 324/762.01 |
| 2013/0190660 | A1 * | 7/2013 | Tanaka | A61B 18/1402 601/2 |
| 2014/0364688 | A1 * | 12/2014 | Wilson | A61B 1/00158 600/102 |
| 2016/0089001 | A1 * | 3/2016 | Hara | A61B 1/00105 600/109 |
| 2016/0220095 | A1 * | 8/2016 | Shimomura | A61B 1/00029 |
| 2016/0324403 | A1 * | 11/2016 | Yeoh | A61B 1/00165 |
| 2016/0330415 | A1 * | 11/2016 | Mizuno | H04N 9/04511 |
| 2017/0025961 | A1 * | 1/2017 | Seeman | H02M 3/1584 |
| 2017/0332888 | A1 * | 11/2017 | Amling | H04N 5/23241 |

FOREIGN PATENT DOCUMENTS

| | | |
|---|---|---|
| JP | 2004-242878 A | 9/2004 |
| JP | 2005-66129 A | 3/2005 |
| JP | 2007-148592 A | 6/2007 |
| WO | 2012/005108 A1 | 1/2012 |
| WO | 2013/128767 A1 | 9/2013 |

* cited by examiner

MEDICAL DEVICE INCLUDING A PATIENT CIRCUIT CONTROLLED BY A SECONDARY CIRCUIT THAT DETECTS ERRONEOUS TRANSMISSION

CROSS-REFERENCE TO RELATED APPLICATION(S)

The present application claims priority to and incorporates by reference the entire contents of Japanese Patent Application No. 2018-039946 filed in Japan on Mar. 6, 2018.

BACKGROUND

The present disclosure relates to a medical device.

In the related art, there is known a configuration including a patient circuit and a secondary circuit in a medical device including an imaging device such as an electronic scope that captures an image of a subject (for example, see Japanese Laid-open Patent Publication No. H2-193634 A, referred to as JPH2-193634 A hereinafter).

According to the technology disclosed in JPH2-193634 A, a secondary circuit and a patient circuit are electrically isolated from each other using an insulation device such as a photocoupler or a high-frequency transformer and are connected to each other.

SUMMARY

When a patient circuit is controlled by a secondary circuit, serial communication is considered to be used. In a case in which the serial communication is used, when noise is superimposed on serial data transmitted from the secondary circuit to the patient circuit via an insulation device due to an influence of disturbance on the insulation device at the time of transmitting the serial data, the following problem may occur.

Serial data received by the patient circuit may become different serial data (data or the like indicating control content (processing content) may become different content due to noise). In other words, erroneous transmission of the serial data from the secondary circuit to the patient circuit may occur. In addition, when the erroneous transmission occurs, the patient circuit may perform an operation that is not intended by the secondary circuit and, in the worst case, an electronic component included in the patient circuit may get out of order.

The following method is considered as a method of detecting the erroneous transmission of the serial data from the secondary circuit to the patient circuit.

After the patient circuit receives serial data, the secondary circuit gives a request for reading the serial data to the patient circuit. Thereafter, the patient circuit reads the received serial data in response to the reading request and transmits the read serial data to the secondary circuit. Then, the secondary circuit compares the serial data transmitted to the patient circuit with the serial data transmitted from the patient circuit to determine whether erroneous transmission occurs.

However, in the above-described method, it is necessary to feed the transmitted serial data back by giving the reading request, and thus delay occurs in the determination of whether the erroneous transmission occurs. Then, when the erroneous transmission occurs, the secondary circuit may perform an unintended operation with respect to the patient circuit before the determination due to the delay and, in the worst case, there is concern of an electronic component included in the patient circuit being broken down.

The present disclosure, which has been made in view of the above-described circumstances, is directed to a medical device.

According to an aspect of the present disclosure, a medical device is provided which includes a first data transmission path that includes a first insulation device connecting a secondary circuit and a patient circuit such that serial data output from the secondary circuit is transmitted to the patient circuit while maintaining electrical insulation between the secondary circuit and the patient circuit; a second data transmission path that includes a second insulation device connecting the secondary circuit and the patient circuit such that the serial data transmitted from the secondary circuit to the patient circuit via the first data transmission path is fed back to the secondary circuit while maintaining electrical insulation between the secondary circuit and the patient circuit; and a comparison determination unit that is provided in the secondary circuit and compares the serial data output from the secondary circuit with the serial data fed back to the secondary circuit.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Hereinafter modes for carrying out the present disclosure (hereinafter referred to as embodiments) will be described with reference to the drawings. The present disclosure is not limited to embodiments to be described below. Further, the same reference numerals are given to the same units in the description of the drawings.

First Embodiment

Schematic Configuration of Endoscope Device

Figure 1:
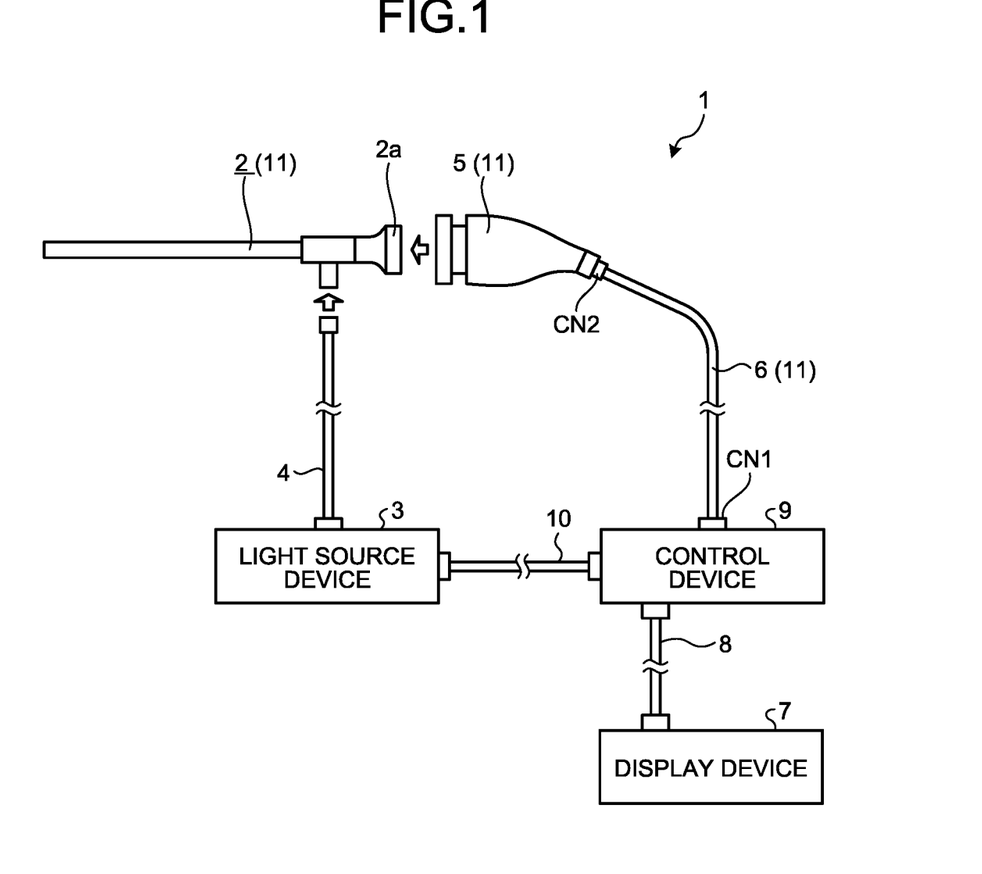
FIG. 1 is a diagram illustrating a schematic configuration of an endoscope device according to a first embodiment.

FIG. 1 is a diagram illustrating a schematic configuration of an endoscope device 1 according to a first embodiment.

The endoscope device 1 corresponds to a medical device according to the present disclosure. The endoscope device 1 is used in medical fields and is a device that observes a subject such as a biological body. The endoscope device 1 includes an insertion unit 2, a light source device 3, a light guide 4, a camera head 5, a first transmission cable 6, a display device 7, a second transmission cable 8, a control device 9, and a third transmission cable 10, as illustrated in FIG. 1.

In the first embodiment, the insertion unit 2 is configured as a rigid endoscope. That is, the insertion unit 2 is of an elongated shape, entirely rigid, and inserted into a living body. Incidentally, a part of the insertion unit 2 may be flexible and the other part thereof may be rigid in other embodiments. The insertion unit 2 includes one or a plurality of lenses that constitute an optical system to condense a subject image.

The light source device 3, to which one end of the light guide 4 is connected, supplies light for illuminating the inside of the living body to the one end of the light guide 4 under the control of the control device 9. Although the light source device 3 is provided separately from the control device 9 in the first embodiment, a control device may be used which a light source device is incorporated therein.

While the one end of the light guide 4 is detachably connected to the light source device 3, the other end thereof is detachably connected to the insertion unit 2. With this, the light guide 4 receives the light at the one end from the light source device 3, and transmits the light therethrough to the other end and thus to the insertion unit 2. The light supplied to the insertion unit 2 is emitted from a distal end of the insertion unit 2 and thus illuminates the living body. The light which has been emitted to the living body and is reflected from the living body is condensed (as a subject image) by the optical system inside the insertion unit 2.

The camera head 5 is detachably connected to a proximal end (an eyepiece 2*a* (see FIG. 1)) of the insertion unit 2. The camera head 5 captures a subject image condensed in the insertion unit 2 and outputs an image signal (RAW signal) obtained through the capturing under the control of the control device 9. In the first embodiment, the image signal is an image signal of 4 K or more.

The first transmission cable 6 includes connectors CN1 and CN2 (see FIG. 1) at corresponding ends. The connector CN1 at one end is detachably connected to the control device 9, and the connector CN2 at the other end is detachably connected to the camera head 5. In addition, the first transmission cable 6 transmits an image signal output from the camera head 5 to the control device 9 and transmits a control signal, a synchronization signal, a clock signal, driving power, and the like output from the control device 9 to the camera head 5.

The transmission of the image signal from the camera head 5 to the control device 9 via the first transmission cable 6 may be realized by an optical signal or by an electric signal. The same applies to the transmission of the control signal, the synchronization signal, and the clock signal from the control device 9 to the camera head 5 via the first transmission cable 6.

The insertion unit 2, the camera head 5, and the first transmission cable 6 described above correspond to an imaging device 11 (see FIG. 1) according to the present disclosure.

The control device 9 corresponds to an image processing device according to the present disclosure. The control device 9 includes a central processing unit (CPU) and the like and comprehensively controls operations of the light source device 3, the camera head 5, and the display device 7.

Specifically, the control device 9 generates a video signal by performing a predetermined process on the image signal acquired from the camera head 5 via the first transmission cable 6 and outputs the video signal to the display device 7 via the second transmission cable 8. Then, the display device 7 displays an image based on the video signal. The control device 9 outputs a control signal or the like to the camera head 5 or the light source device 3 via the first transmission cable 6 and the third transmission cable 10.

One end of the third transmission cable 10 is detachably connected to the light source device 3 and the other end thereof is detachably connected to the control device 9. Then, the third transmission cable 10 transmits a control signal from the control device 9 to the light source device 3.

Secondary Circuit and Patient Circuit

Figure 2:
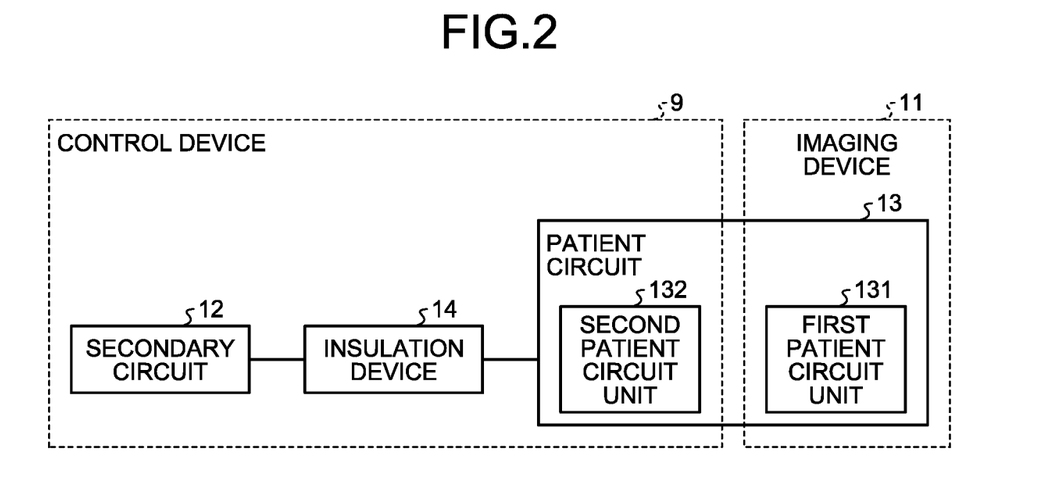
FIG. 2 is a diagram illustrating a secondary circuit and a patient circuit in the endoscope device.

FIG. 2 is a diagram illustrating a secondary circuit 12 and a patient circuit 13 in the endoscope device 1.

The secondary circuit 12 is provided inside the control device 9 and is protectively grounded. As the secondary circuit 12, for example, a signal processor (not illustrated) may be exemplified which performs a predetermined process on the image signal acquired from the camera head 5 or a control unit 121 (see FIG. 3) that controls the patient circuit 13, or the like. The configuration of the control unit 121 will be described below.

The patient circuit 13 is an electric circuit in which a biological body itself serves as a part of this circuit when the imaging device 11 comes into contact with the biological body, and is a floating circuit that is not protectively grounded. The patient circuit 13 is electrically insulated from the secondary circuit 12. The secondary circuit 12 and the patient circuit 13 are connected via an insulation device 14.

As illustrated in FIG. 2, the patient circuit 13 includes a first patient circuit unit 131 that is provided in the imaging device 11 and a second patient circuit unit 132 that is provided inside the control device 9 and is electrically connected to the first patient circuit unit 131 when the imaging device 11 is connected to the control device 9.

As the first patient circuit unit 131, an image sensor (not illustrated) such as a charge coupled device (CCD) or a complementary metal oxide semiconductor (CMOS) that captures a subject image condensed in the insertion unit 2, a heater that generates heat by conduction and prevents clouding occurring in an optical system inside the insertion unit 2 by applying the heat to the optical system, or the like can be exemplified.

Figure 3:
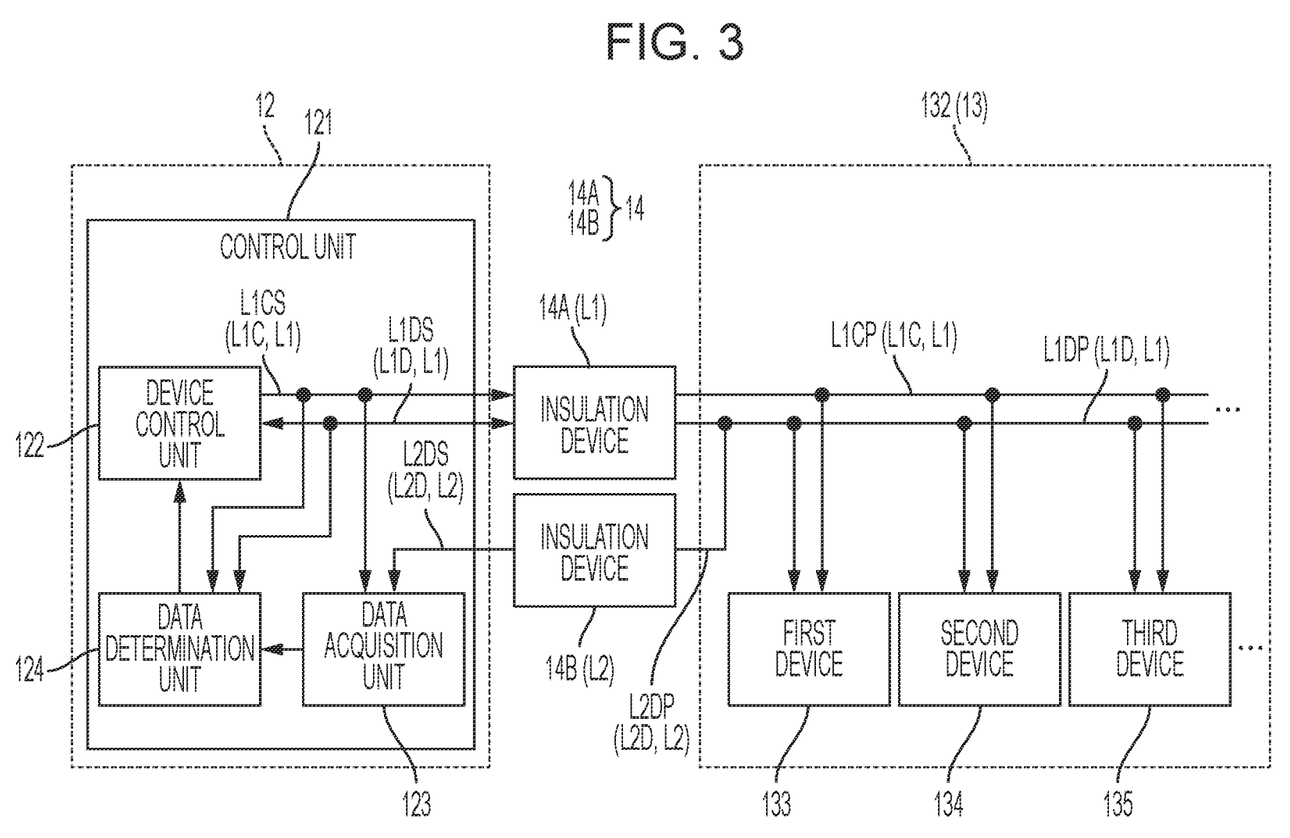
FIG. 3 is a block diagram illustrating a control structure of the patient circuit in the secondary circuit.

As the second patient circuit unit 132, a first device 133 to a third device 135 (see FIG. 3) that perform various processes under the control of the control unit 121, a plurality of regulators (not illustrated) each generating a power voltage necessary to drive the above-described image sensor based on the driving power supplied from a primary circuit (not illustrated) and supplying the power voltage to the image sensor, or the like can be exemplified. In FIG. 3, three devices, that is, the first device 133 to the third device 135 are illustrated for convenience of description, but the number of devices that perform various processes under the control of the control unit 121 is not limited to three, and another number of devices may be provided. The configurations of the first device 133 to the third device 135 will be described below.

Here, as the insulation device 14, a photocoupler, a high-frequency transformer, a digital isolation device, or the like can be exemplified. Between the secondary circuit 12 and the patient circuit 13, an image signal, a control signal, a synchronization signal, a clock signal, and the like are transmitted via the insulation device 14.

Control Structure of Patient Circuit in Secondary Circuit

Next, a control structure of the patient circuit 13 by the secondary circuit 12 will be described.

FIG. 3 is a block diagram illustrating a control structure of the patient circuit 13 in the secondary circuit 12.

In the first embodiment, a structure in which the patient circuit 13 (the first device 133 to the third device 135) is controlled by the secondary circuit 12 (the control unit 121) using serial communication of the inter-integrated circuit (I2C) standard is adopted. More specifically, the first device 133 to the third device 135 function as slave devices and are connected in a party line configuration via the insulation device 14, a first signal line L1C, and a second signal line L1D to the control unit 121 (a device control unit 122 (see FIG. 3)) that functions as a master device (see FIG. 3). In the first embodiment, the insulation device 14 has three channels. The first signal line L1C is connected to one channel among the three channels in the insulation device 14. The second signal line L1D is connected to one of two channels to which the first signal line L1C is not connected among the three channels in the insulation device 14.

The first signal line L1C is a signal line that transmits a clock signal. The second signal line L1D is a signal line that transmits serial data. The insulation device 14, the first signal line L1C, and the second signal line L1D correspond to a first data transmission path L1 that goes through a first insulation device 14A (see FIG. 3) according to the present disclosure. Hereinafter, for convenience of description, in the first signal line L1C, a signal line on the side of the secondary circuit 12 is referred to as a secondary-side first signal line L1CS (see FIG. 3) and a signal line on the side of the patient circuit 13 is referred to as a patient-side first signal line L1CP (see FIG. 3). Similarly, in the second signal line L1D, a signal line on the side of the secondary circuit 12 is referred to as a secondary-side second signal line L1DS (see FIG. 3) and a signal line on the side of the patient circuit 13 is referred to as a patient-side second signal line L1DP (see FIG. 3).

The first device 133 to the third device 135 correspond to a plurality of processors according to the present disclosure. The first device 133 to the third device 135 receive the same serial data (control signal) as the serial data output from the device control unit 122 via the insulation device 14 and the second signal line L1D based on the same clock signal as the clock signal output from the device control unit 122 via the insulation device 14 and the first signal line L1C. Here, each of the first device 133 to the third device 135 has an address. The serial data includes the address in addition to data indicating control content (processing content). Therefore, of the first device 133 to the third device 135, only the device that has the address included in the serial data performs a process in accordance with the data (the control content (processing content)) included in the serial data.

Here, as the first device 133 to the third device 135, an analog-to-digital (AD) converter, a digital-to-analog (DA) converter, a serial/parallel converter, or the like can be exemplified. Incidentally, the first device 133 to the third device 135 are not limited to an AD converter, a DA converter, and a serial/parallel converter, but other devices may be adopted as long as the devices are semiconductor devices that perform serial communication.

For example, the AD converter is used to detect the above-described type of images sensor included in the imaging device 11 when the imaging device 11 is connected to the control device 9.

For example, the DA converter is used to perform conduction control of the above-described heater included in the first patient circuit unit 131.

For example, the serial/parallel converter includes an I/O expander and is used to perform ON/OFF control of a power voltage supplied from the plurality of regulators included in the second patient circuit unit 132 to the above-described image sensor included in the first patient circuit unit 131.

The control unit 121 includes, for example, a field programmable gate array (FPGA) which is one kind of programmable integrated circuit. As illustrated in FIG. 3, the control unit 121 includes a device control unit 122, a data acquisition unit 123, and a data determination unit 124.

The device control unit 122 is a unit that performs serial communication with the first device 133 to the third device 135 via the first data transmission path L1. That is, the device control unit 122 outputs a clock signal to the first device 133 to the third device 135 via the first insulation device 14A and the first signal line L1C, and outputs serial data to the first device 133 to the third device 135 via the first insulation device 14A and the second signal line L1D.

As illustrated in FIG. 3, the data acquisition unit 123 is connected to the patient-side second signal line L1DP via the second data transmission path L2 that goes through a second insulation device 14B. The data acquisition unit 123 inputs a clock signal output from the device control unit 122 via the secondary-side first signal line L1CS. Then, the data acquisition unit 123 acquires serial data output from the device control unit 122 to the first device 133 to the third device 135 via the second data transmission path L2 based on the clock signal. That is, the serial data output from the device control unit 122 to the first device 133 to the third device 135 via the first data transmission path L1 is fed back to the secondary circuit 12 via the second data transmission path L2 by the data acquisition unit 123. Hereinafter, for convenience of description, the serial data fed back to the secondary circuit 12 is referred to as fed-back serial data. In addition, serial data which is output from the device control unit 122 and is not transmitted to the side of the patient circuit 13 (still on the side of the secondary circuit 12) is referred to as output serial data. Then, the data acquisition unit 123 outputs the fed-back serial data to the data determination unit 124.

Here, the second data transmission path L2 includes the second insulation device 14B and a third signal line L2D that is connected to one remaining channel to which the first signal line L1C and the second signal line L1D are not connected among the three channels in the insulation device 14. Hereinafter, for convenience of description, in the third signal line L2D, a signal line on the side of the secondary circuit 12 is referred to as a secondary-side third signal line L2DS (see FIG. 3) and a signal line on the side of the patient circuit 13 is referred to as a patient-side third signal line L2DP (see FIG. 3).

That is, in the first embodiment, the first data transmission path L1 and the second data transmission path L2 include the common insulation device 14. The insulation device 14 corresponds to the first and second insulation devices 14A, 14B according to the present disclosure.

The data determination unit 124 corresponds to a comparison determination unit according to the present disclosure. As illustrated in FIG. 3, the data determination unit 124 inputs a clock signal output from the device control unit 122 via the secondary-side first signal line L1CS. The data determination unit 124 inputs the output serial data via the secondary-side second signal line L1DS. The data determination unit 124 digitally compares the output serial data with the fed-back serial data from the data acquisition unit 123 for each bit based on the clock signal to determine whether the serial data received by the first device 133 to the third device 135 becomes different serial data (or whether data or the like indicating control content (processing content) becomes different content due to noise) (or whether erroneous transmission occurs). The data determination unit 124 outputs the determination result to the device control unit 122.

The device control unit 122, for example, retransmits the serial data or shuts down power of the endoscope device 1 when the data determination unit 124 determines that the erroneous transmission occurs.

According to the above-described first embodiment, it is possible to obtain the following advantage.

The endoscope device 1 according to the first embodiment includes the second data transmission path L2 that includes the insulation device 14 between the secondary circuit 12 and the patient circuit 13. The second data transmission path L2 allows the serial data which has been transmitted from the secondary circuit 12 to the patient circuit 13 via the first data transmission path L1 to be fed back to the secondary circuit 12. The endoscope device 1 further includes the data determination unit 124 that compares the output serial data with the fed-back serial data to determine whether erroneous transmission occurs.

Therefore, for example, it is possible to detect whether noise is superimposed on the serial data transmitted to the patient circuit 13 due to an influence of disturbance on the insulation device 14, that is, whether erroneous transmission occurs. Since the serial data transmitted to the patient circuit 13 is fed back to the secondary circuit 12 via the second data transmission path L2, it is not necessary for the secondary circuit 12 (the device control unit 122) to request the patient circuit 13 (the first device 133 to the third device 135) to read the received serial data. That is, delay does not occur in the determination of whether the erroneous transmission occurs.

Accordingly, in the endoscope device 1 according to the first embodiment, it is possible to obtain the advantage that the erroneous transmission of the serial data can be detected satisfactorily.

Here, as the influence of disturbance on the insulation device 14, an influence by use of a treatment tool such as an electric knife, an influence by static electricity, an influence by switching noise at the time of an operation, or an influence from the light source device 3 at the time of an operation, or the like can be exemplified.

In the endoscope device 1 according to the first embodiment, the first data transmission path L1 is a data transmission path of the I2C standard.

Therefore, for example, it is possible to achieve simplification of the structure since the number of channels of the insulation device 14 can be reduced, compared to a case in which the first data transmission path L1 is set as a transmission path of the serial peripheral interface (SPI) standard.

In the endoscope device 1 according to the first embodiment, the first device 133 to the third device 135 include the serial/parallel converter.

Incidentally, the serial data (data indicating the control content (processing content)) transmitted to the serial/parallel converter by the device control unit 122 is data indicating a supplying sequence of a power voltage from the plurality of regulators included in the second patient circuit unit 132 to the above-described image sensor included in the first patient circuit unit 131. The serial/parallel converter performs ON/OFF control of the power voltage supplied from the plurality of regulators to the image sensor in accordance with the supplying sequence.

Here, when erroneous transmission of the serial data to the serial/parallel converter occurs, the supplying sequence included in the serial data may be different from the supplying sequence intended by the device control unit 122. When the power voltage is supplied to the image sensor in accordance with the different supplying sequence, the image sensor may be broken down in the worst case.

Accordingly, the control unit 121 quickly determines whether erroneous transmission occurs as described above. Thus, when the erroneous transmission occurs, the above-described image sensor can be prevented from being broken down, for example, by shutting down the power of the endoscope device 1.

In the endoscope device 1 according to the first embodiment, the first device 133 to the third device 135 include the AD converter.

Incidentally, when erroneous transmission of the serial data to the AD converter occurs, erroneous detection may occur at the time of detecting the above-described type of image sensor using the AD converter.

Here, the device control unit 122 receives the serial data including the type of image sensor from the AD converter via the first data transmission path L1. Thereafter, the device control unit 122 selects a supplying sequence of the power voltage corresponding to the type of image sensor and transmits the serial data including the selected supplying sequence to the above-described serial/parallel converter via the first data transmission path L1. That is, when the type of image sensor is erroneously detected, a wrong supplying sequence may be transmitted to the serial/parallel converter.

Accordingly, the control unit 121 quickly determines whether erroneous transmission occurs, as described above. Thus, when the erroneous transmission occurs, the type of the image sensor can be correctly detected using the AD converter, for example, by retransmitting the serial data. Therefore, it is possible to avoid transmitting the wrong supplying sequence to the serial/parallel converter.

In the endoscope device 1 according to the first embodiment, the first data transmission path L1 and the second data transmission path L2 include the common insulation device 14.

Therefore, it is possible to achieve the simplification and miniaturization of the structure, for example, compared to a case in which separate insulation devices are provided in the first data transmission path L1 and the second data transmission path L2.

The endoscope device 1 according to the first embodiment includes the data acquisition unit 123 that acquires the serial data transmitted from the secondary circuit 12 to the patient circuit 13 via the first data transmission path L1, and outputs the acquired serial data to the data determination unit 124.

Therefore, the data determination unit 124 can digitally compare the output serial data with the fed-back serial data for each bit to determine whether erroneous transmission occurs. That is, the data determination unit 124 can determine how the serial data becomes wrong. Then, for example, when only data at a bit position of the least significant bit of the serial data is wrong, the device control unit 122 can perform control such that the serial data is not retransmitted since the degree of influence on the serial data is low.

Second Embodiment

Next, a second embodiment will be described.

In the following description, the same reference numerals are given to the same configurations as those of the above-described first embodiment and the detailed description will omitted or simplified.

Figure 4:
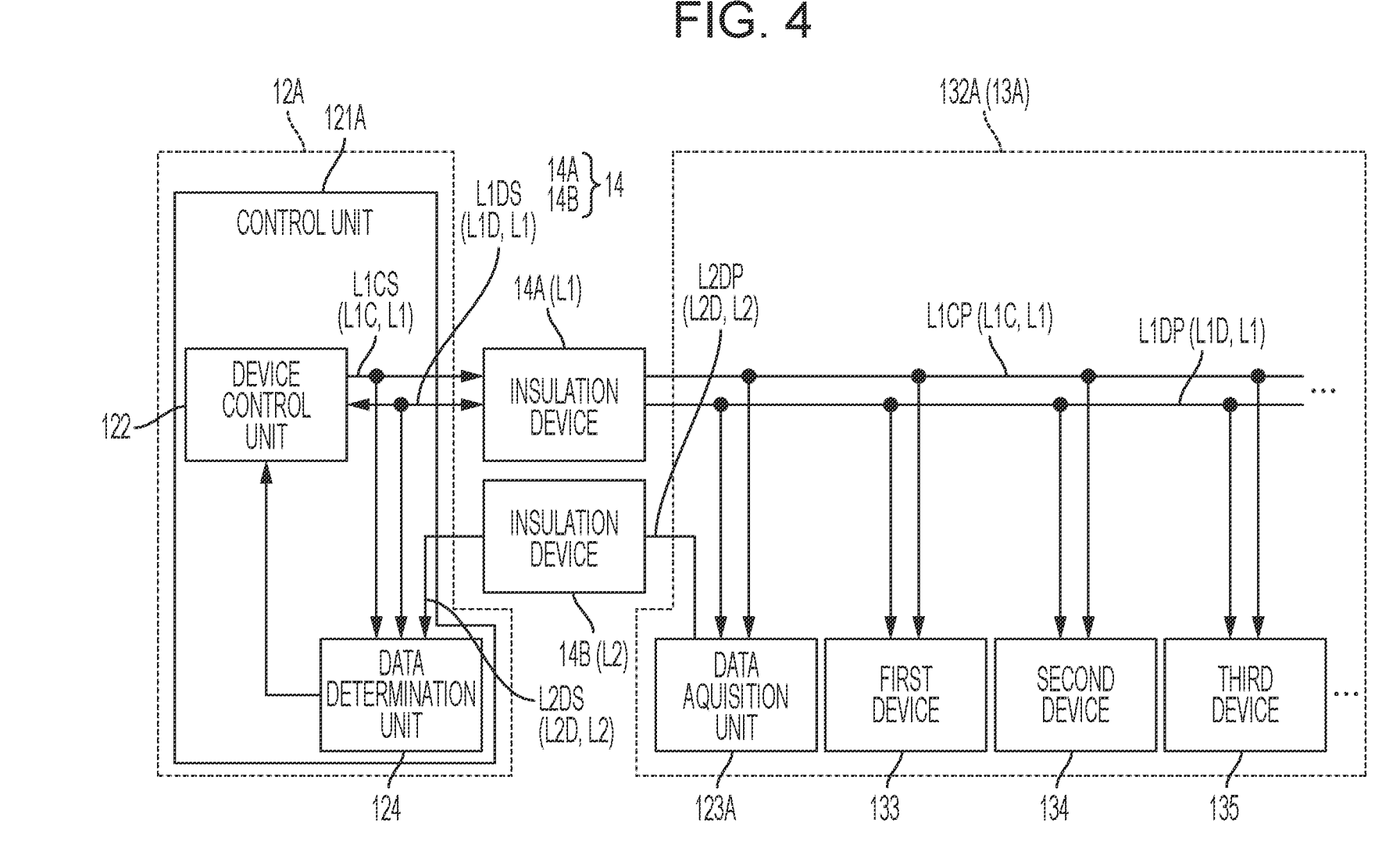
FIG. 4 is a block diagram illustrating a control structure of a patient circuit in a secondary circuit according to a second embodiment.

FIG. 4 is a diagram corresponding to FIG. 3 and is a block diagram illustrating a control structure of a patient circuit 13A in a secondary circuit 12A according to the second embodiment.

In the second embodiment, the function of the data acquisition unit 123 is provided in the patient circuit 13 (the second patient circuit unit 132) unlike the above-described first embodiment.

Hereinafter, for convenience of description, a secondary circuit (the control unit) according to the second embodiment is referred to as the secondary circuit 12A (the control unit 121A) (see FIG. 4). A patient circuit (second patient circuit unit) according to the second embodiment is referred to as the patient circuit 13A (a second patient circuit unit 132A) (see FIG. 4). Further, a data acquisition unit according to the second embodiment is referred to as a data acquisition unit 123A (see FIG. 4).

As illustrated in FIG. 4, the data acquisition unit 123A is connected in a party line configuration to the device control unit 122 via the first data transmission path L1 as in the first device 133 to the third device 135. The data acquisition unit 123A receives serial data output from the device control unit 122 via the first insulation device 14A and the second signal line L1D based on a clock signal output from the device control unit 122 via the first insulation device 14A and the first signal line L1C as with the first device 133 to the third device 135.

Here, as illustrated in FIG. 4, the data acquisition unit 123A is connected to the data determination unit 124 via the second data transmission path L2. Then, the data acquisition unit 123A outputs the received serial data to the data determination unit 124 via the second data transmission path L2.

As the above-described data acquisition unit 123A, a flip-flop or the like can be exemplified.

As illustrated in FIG. 4, the control unit 121A is different from the control unit 121 described in the above-described first embodiment in that the data acquisition unit 123 is omitted and the data determination unit 124 is connected to the data acquisition unit 123A via the second data transmission path L2.

As with the above-described first embodiment, the data determination unit 124 digitally compares the output serial data with the fed-back serial data from the data acquisition unit 123A for each bit based on the clock signal to determine whether erroneous transmission occurs. As with the above-described first embodiment, the device control unit 122, for example, retransmits the serial data or shuts down the power of the endoscope device 1 when the data determination unit 124 determines that the erroneous transmission occurs.

As described in the second embodiment, it is possible to obtain the same advantage as that of the above-described first embodiment even when the data acquisition unit 123A is provided in the patient circuit 13A.

Third Embodiment

Next, a third embodiment will be described.

In the following description, the same reference numerals are given to the same configurations as those of the above-described first embodiment and the detailed description will omitted or simplified.

Figure 5:
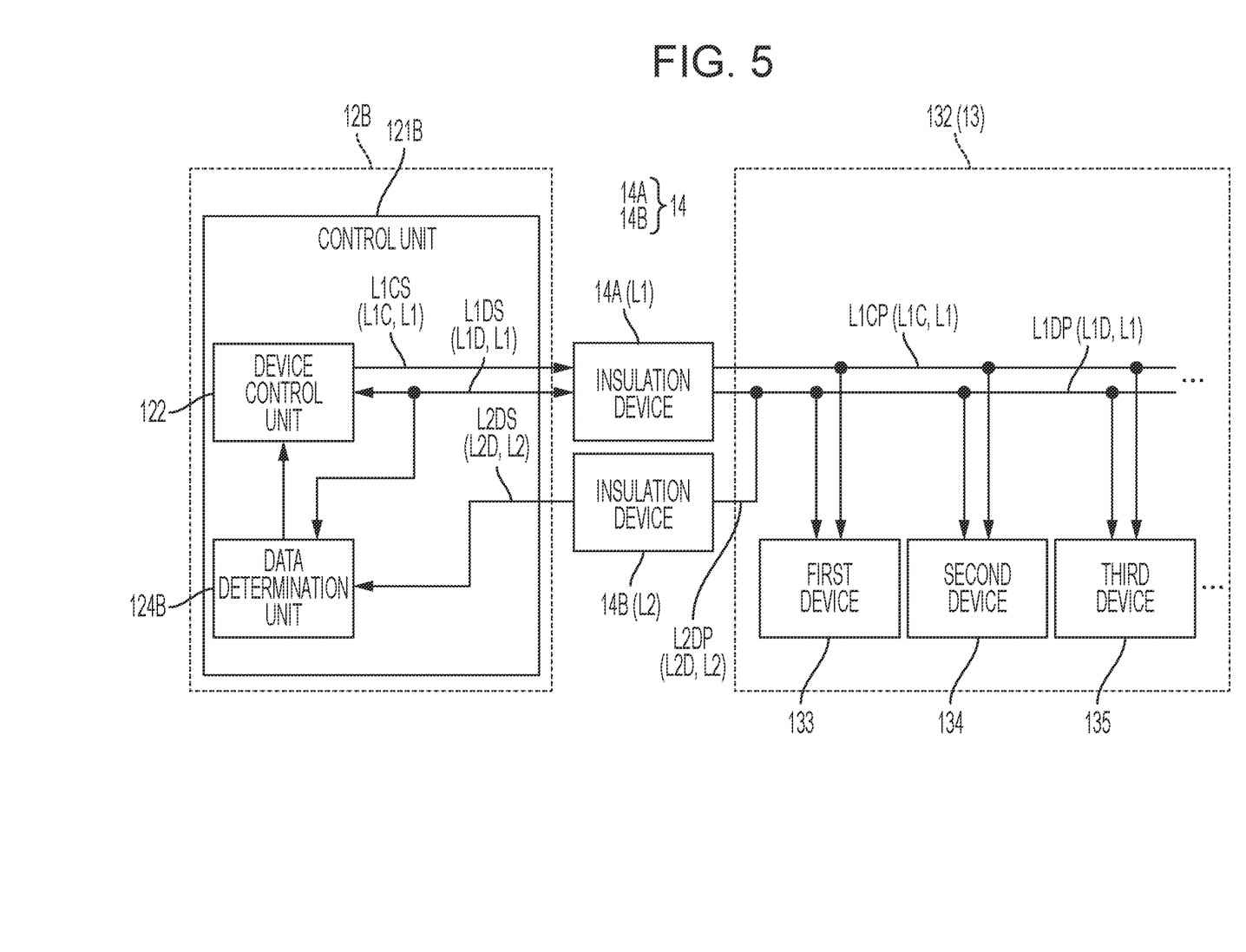
FIG. 5 is a block diagram illustrating a control structure of a patient circuit in a secondary circuit according to a third embodiment.

FIG. 5 is a diagram corresponding to FIG. 3 and is a block diagram illustrating a control structure of the patient circuit 13 in a secondary circuit 12B according to the third embodiment.

In the third embodiment, the function of the data acquisition unit 123 in the above-described first embodiment is omitted.

Hereinafter, for convenience of description, a secondary circuit (control unit) according to the third embodiment is referred to as the secondary circuit 12B (a control unit 121B) (see FIG. 5). A data determination unit according to the third embodiment is referred to as a data determination unit 124B (see FIG. 5).

As illustrated in FIG. 5, the control unit 121B is different from the control unit 121 described in the above-described first embodiment in that the data acquisition unit 123 is omitted and the data determination unit 124B is connected to the patient-side second signal line L1DP via the second data transmission path L2. That is, serial data output from the device control unit 122 is fed back to the data determination unit 124B via the second data transmission path L2.

The data determination unit 124B corresponds to a comparison determination unit according to the present disclosure. As illustrated in FIG. 5, the data determination unit 124B inputs the output serial data via the secondary-side second signal line L1DS. The data determination unit 124B inputs the fed-back serial data via the second data transmission path L2. Then, the data determination unit 124B compares a waveform of the output serial data with a waveform of the fed-back serial data in an analog manner to determine whether the serial data received by the first device 133 to the third device 135 becomes different serial data (or data or the like indicating control content (processing content) becomes different content due to noise) (or whether erroneous transmission occurs). The device control unit 122, for example, retransmits the serial data or shuts down the power of the endoscope device 1 when the data determination unit 124B determines that the erroneous transmission occurs as in the above-described first embodiment.

Figure 6A:
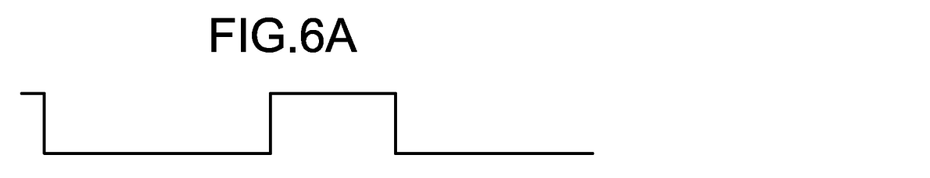
FIGS. 6A to 6C are diagrams illustrating a method of determining erroneous transmission by a data determination unit.
Figure 6B:
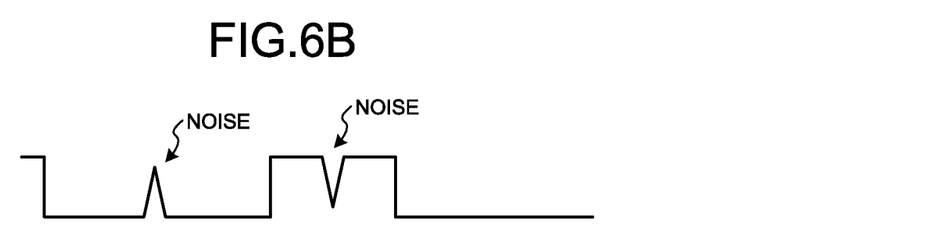
Figure 6C:
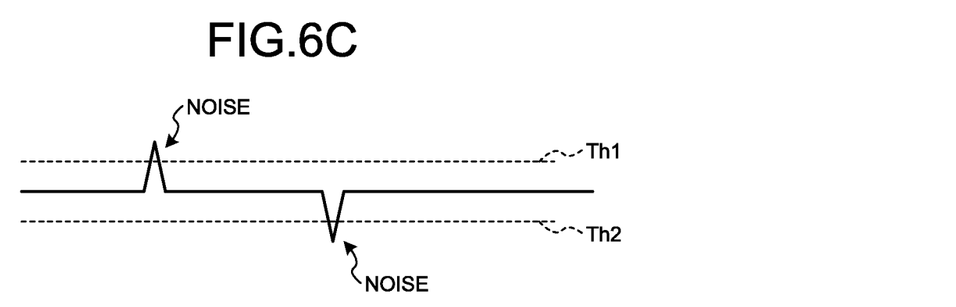

FIGS. 6A to 6C are diagrams illustrating a method of determining erroneous transmission by the data determination unit 124B. Specifically, FIG. 6A is a diagram illustrating a waveform of the output serial data. FIG. 6B is a diagram illustrating a waveform of the fed-back serial data when noise is superimposed on the serial data. FIG. 6C is a diagram illustrating a process by the data determination unit 124B.

Specifically, the data determination unit 124B obtains a difference between the input output serial data (see FIG. 6A) and the fed-back serial data (see FIG. 6B), as illustrated in FIG. 6C. Then, the data determination unit 124B compares the value of the obtained difference with predetermined thresholds Th1 and Th2. When the value of the obtained difference is out of a range between the thresholds Th1 and Th2, the data determination unit 124B determines that the erroneous transmission occurs.

As the above-described data determination unit 124B, a comparator or the like can be exemplified.

Even when the data acquisition unit 123 is omitted and the waveforms of the output serial data and the fed-back serial data are compared with each other in the analog manner to determine whether the erroneous transmission occurs as in the above-described third embodiment, it is possible to obtain the same advantages as those of the above-described first embodiment.

Modifications

The modes for carrying out the present disclosure have been described above, but the present disclosure is not limited to the above-described first to third embodiments.

In the above-described first to third embodiments, the first data transmission path L1 and the second data transmission path L2 include the common insulation device 14, but the present disclosure is not limited thereto. For example, a configuration in which separate insulation devices are provided in the first data transmission path L1 and the second data transmission path L2 may be adopted.

In the above-described first to third embodiments, the first data transmission path L1 is the data transmission path of the I2C standard, but the present disclosure is not limited thereto. For example, the first data transmission path L1 may be a data transmission path of the SPI standard.

In the above-described first to third embodiments, the medical device according to the present disclosure is configured as the endoscope device 1 in which the rigid endoscope (the insertion unit 2) is used, but the present disclosure is not limited thereto. For example, the medical device according to the present disclosure may be configured as an endoscope device in which a flexible endoscope is used, an ultrasonic diagnostic diagnosis system in which an ultrasonic wave is used, an energy treatment system in which energy is given to a subject for treatment by the energy, or an X-ray device in which an X-ray is used.

In the medical device according to the disclosure, it is possible to obtain the advantage that erroneous transmission of serial data can be detected satisfactorily.

Although the disclosure has been explained with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical device comprising:
a first data transmission path that includes a first insulator connecting a secondary circuit and a patient circuit such that serial data output from the secondary circuit is transmitted to the patient circuit while maintaining electrical insulation between the secondary circuit and the patient circuit; and
a second data transmission path that includes a second insulator connecting the secondary circuit and the patient circuit such that the serial data transmitted from the secondary circuit to the patient circuit via the first data transmission path is fed back to the secondary circuit while maintaining electrical insulation between the secondary circuit and the patient circuit as fed-back serial data, wherein
the secondary circuit includes comparison circuitry that compares the serial data output from the secondary circuit with the fed-back serial data,
a sensor that captures an image of a subject and outputs an image signal; and
an image processor to which the sensor is detachably connected and which processes the image signal from the sensor,
wherein the sensor includes a first patient circuit that is part of the patient circuit, and
wherein the image processor includes
a second patient circuit that is part of the patient circuit and is electrically connected to the first patient circuit when the sensor is connected to the image processor, and the secondary circuit.

2. The medical device according to claim 1,
wherein the patient circuit includes a plurality of processors each of which receives the same serial data as the serial data transmitted from the secondary circuit via the first data transmission path.

3. The medical device according to claim 2,
wherein the first data transmission path is compliant with Inter-Integrated Circuit standard.

4. The medical device according to claim 1,
wherein the first insulator and the second insulator are a single insulator, and
wherein the first data transmission path and the second data transmission path include a common insulator.

5. The medical device according to claim 1, further comprising
data acquisition circuitry configured to acquire the serial data transmitted from the secondary circuit to the patient circuit via the first data transmission path and outputs acquired serial data to the comparison circuitry.

6. The medical device according to claim 5,
wherein the data acquisition circuitry is in the secondary circuit, and the data acquisition circuitry is configured to acquire, via the second data transmission path, the serial data transmitted from the secondary circuit to the patient circuit via the first data transmission path, and output the acquired serial data to the comparison circuitry.

7. A medical device comprising:
a first data transmission path that includes a first insulator connecting a secondary circuit and a patient circuit such that serial data output from the secondary circuit is transmitted to the patient circuit while maintaining electrical insulation between the secondary circuit and the patient circuit; and
a second data transmission path that includes a second insulator connecting the secondary circuit and the patient circuit such that the serial data transmitted from the secondary circuit to the patient circuit via the first data transmission path is fed back to the secondary circuit while maintaining electrical insulation between the secondary circuit and the patient circuit as fed-back serial data, wherein
the secondary circuit includes comparison circuitry that compares the serial data output from the secondary circuit with the fed-back serial data,
the patient circuit includes a plurality of processors each of which receives the same serial data as the serial data transmitted from the secondary circuit via the first data transmission path, and
the plurality of processors include a serial/parallel converter.

8. The medical device according to claim 7,
wherein the plurality of processors include an analog-to-digital converter.

9. The medical device according to claim 7,
wherein the first insulator and the second insulator are a single insulator, and
wherein the first data transmission path and the second data transmission path include a common insulator.

10. The medical device according to claim 7, further comprising
data acquisition circuitry configured to acquire the serial data transmitted from the secondary circuit to the patient circuit via the first data transmission path and outputs acquired serial data to the comparison circuitry.

11. The medical device according to claim 10, wherein the data acquisition circuitry is in the secondary circuit, and the data acquisition circuitry is configured to acquire, via the second data transmission path, the serial data transmitted from the secondary circuit to the patient circuit via the first data transmission path, and output the acquired serial data to the comparison circuitry.

12. The medical device according to claim 7, further comprising:
a sensor that captures an image of a subject and outputs an image signal; and
an image processor to which the sensor is detachably connected and which processes the image signal from the sensor,
wherein the sensor includes a first patient circuit that is part of the patient circuit, and
wherein the image processor includes
a second patient circuit that is part of the patient circuit and is electrically connected to the first patient circuit when the sensor is connected to the image processor, and
the secondary circuit.

13. A medical device comprising:
a first data transmission path that includes a first insulator connecting a secondary circuit and a patient circuit such that serial data output from the secondary circuit is transmitted to the patient circuit while maintaining electrical insulation between the secondary circuit and the patient circuit; and
a second data transmission path that includes a second insulator connecting the secondary circuit and the patient circuit such that the serial data transmitted from the secondary circuit to the patient circuit via the first data transmission path is fed back to the secondary circuit while maintaining electrical insulation between the secondary circuit and the patient circuit as fed-back serial data, wherein the secondary circuit includes comparison circuitry that compares the serial data output from the secondary circuit with the fed-back serial data,
the patient circuit includes a plurality of processors each of which receives the same serial data as the serial data transmitted from the secondary circuit via the first data transmission path, and
the plurality of processors include an analog-to-digital converter.

14. The medical device according to claim 13,
wherein the first insulator and the second insulator are a single insulator, and
wherein the first data transmission path and the second data transmission path include a common insulator.

15. The medical device according to claim 13, further comprising
data acquisition circuitry configured to acquire the serial data transmitted from the secondary circuit to the patient circuit via the first data transmission path and outputs acquired serial data to the comparison circuitry.

16. The medical device according to claim 15, wherein the data acquisition circuitry is in the secondary circuit, and the data acquisition circuitry is configured to acquire, via the second data transmission path, the serial data transmitted from the secondary circuit to the patient circuit via the first data transmission path, and output the acquired serial data to the comparison circuitry.

17. The medical device according to claim 13, further comprising:
a sensor that captures an image of a subject and outputs an image signal; and
an image processor to which the sensor is detachably connected and which processes the image signal from the sensor,
wherein the sensor includes a first patient circuit that is part of the patient circuit, and
wherein the image processor includes
a second patient circuit that is part of the patient circuit and is electrically connected to the first patient circuit when the sensor is connected to the image processor, and
the secondary circuit.

* * * * *